United States Patent [19]

Savitt et al.

[11] Patent Number: 5,133,336

[45] Date of Patent: Jul. 28, 1992

[54] DISPOSABLE LIQUID SUPPLY SYSTEM FOR USE IN AN ENDOSCOPE

[75] Inventors: Robert Savitt, Dover Plains; Christopher O. R. Siddall, Rye, both of N.Y.

[73] Assignee: Endoscopy Support Services, Inc., Patterson, N.Y.

[21] Appl. No.: 601,968

[22] Filed: Oct. 22, 1990

[51] Int. Cl.⁵ ............................................. A61B 1/12
[52] U.S. Cl. .............................................. 128/4
[58] Field of Search ................................. 128/4, 6

[56] References Cited

U.S. PATENT DOCUMENTS

| | | | |
|---|---|---|---|
| 4,325,362 | 4/1982 | Ouchi et al. | 128/4 A |
| 4,552,130 | 11/1985 | Kino Shita | 128/4 A |
| 4,748,970 | 6/1988 | Nakajima | 128/4 A |
| 4,760,838 | 8/1988 | Fukuda | 128/4 A |
| 4,800,869 | 1/1989 | Nakajima | 128/4 A |
| 4,844,052 | 7/1989 | Iwakoshi et al. | 128/4 |
| 4,860,731 | 8/1989 | Matsuura | 128/4 X |
| 4,901,142 | 2/1990 | Ikuno et al. | 128/4 |
| 4,973,311 | 11/1990 | Iwakoshi et al. | 128/4 |

Primary Examiner—Gene Mancene
Assistant Examiner—Thomas Price
Attorney, Agent, or Firm—Sprung Horn Kramer & Woods

[57] ABSTRACT

A disposable liquid supply system comprises a closed liquid container, a first flexible tube connected to the container and terminating at the top thereof for introducing a gas into the container, and a second flexible tube connected to the container and terminating at the bottom thereof for supplying a liquid to an endoscope. The container which contains a desired liquid, and the first and second tubes form a disposable, closed sealed unit which is connectable to an endoscope prior to use.

32 Claims, 12 Drawing Sheets

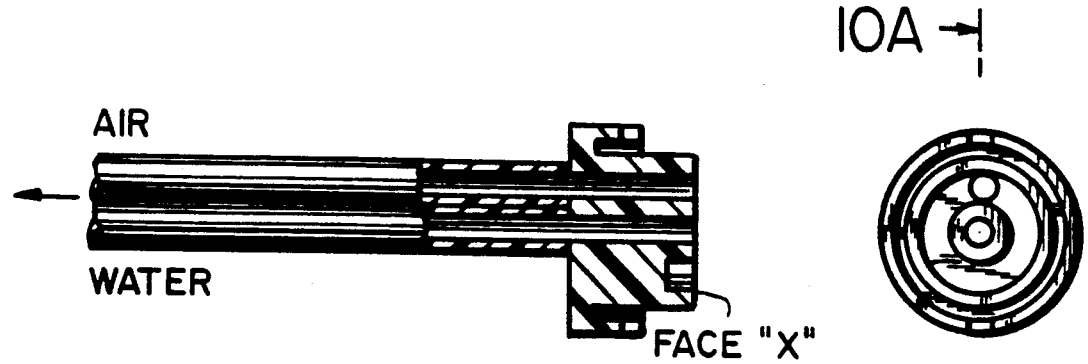
FIG.10A
FIG.10B
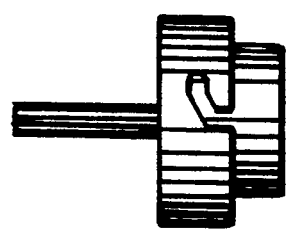
FIG.10C
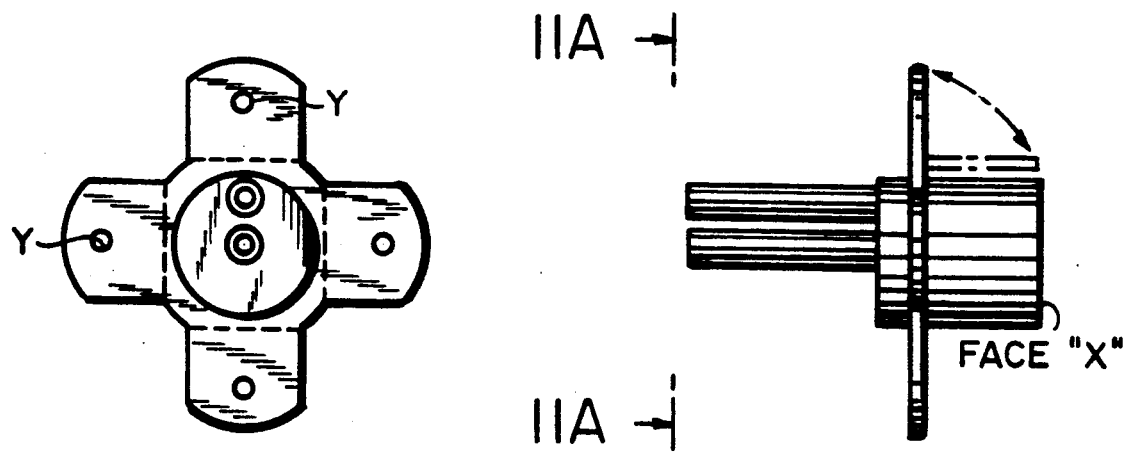
FIG.11A
FIG.11B

DISPOSABLE LIQUID SUPPLY SYSTEM FOR USE IN AN ENDOSCOPE

BACKGROUND OF THE INVENTION

The present invention relates to an endoscope and, more particularly, to a disposable liquid supply system for use with an endoscope.

The development of endoscopic instruments has greatly enhanced our ability to diagnose and treat diseases in relatively inaccessible regions of the body. The first examinations that could be considered "endoscopic" in the modern sense were probably the rectal inspections conducted in the 18th century. The physician peered through a rigid tube inserted into the patient's rectum and relied on candles or gas lamps to illuminate the interior. By today's standards the physician saw very little; however, endoscopic examinations continued and endoscopes of various designs were invented.

In 1932, Schindler introduced the semi-flexible gastroscope. This device was easier and safer to insert than prior endoscopes, and it offered sharper images and a wider field of view allowing visualization of about seventy-five percent of the gastric mucosa. The instrument could also be fitted with a camera and with a channel for the insertion of biopsy forceps. The Schindler semi-flexible endoscope was used until the late 1950's.

Although accessories for the semi-flexible instruments were continually improved, the landmark development in endoscopy was the incorporation of fiberoptic principles into endoscopic design. Hirschowitz produced the first fiberoptic gastroscope in 1958. This completely flexible instrument was inserted with much less discomfort to the patient. Because of its maneuverability, it could reveal a duodenum and other areas that were previously inaccessible to rigid endoscopes.

The two outstanding features of the fiberoptic endoscope are its flexibility and excellent viewing ability. Light travels down the individual glass fibers and emerges at the distal end hardly diminished in intensity. There, a lens system focuses the light and fuses the image, and a set of 20,000 to 30,000 integrated fibers returns the image to the proximal end of the instrument, where the image is magnified. With fiberoptic endoscopes, images are not reversed. The "cold" illumination, produced by filtering out the heat component of the light, does not harm the organ being visualized. The light sources are also adaptable for both movie and still photography and for electronic video recording.

The development of the endoscope will continue indefinitely. The fiberoptic technology is now being replaced in some cases by a direct video imaging system which includes a CCD camera at the distal end of the endoscope tube. This arrangement is an expansion and it permits a reduction in the diameter of the tube.

As is well known, endoscope tubes also include mechanisms for turning the tip in four directions (up, down and to each side) to facilitate passage of the instrument around angles and allow visualization of all surfaces. An additional viewing channel, coupled to a separate eye piece, for simultaneous, direct viewing by a second observer is also available. In addition, the tubes contain channels for air insufflation, water instillation (so that lenses can be cleaned during a procedure) and to allow passage of biopsy instruments and fulguration instruments. Tube channels may also be provided for passage of laser beam devices, spray catheters and polypectomy snare wires.

A typical endoscope, as found in a physician's office or hospital, is used repeatedly over the course of a given day. The endoscope tube must be completely sterilized between each use to avoid the transmission of diseases, such as AIDS, Hepatitis, etc. Typically, a sterilization fluid is passed through the water and air ducts of the instrument to sterilize the internal surfaces. This sterilization fluid is at times supplied from a bottle which temporarily replaces the water bottle used with the endoscope.

Until now, the water supply for an endoscope has comprised a separate, sterilizable water bottle which is removably attached to the endoscope control unit and connected by separate air and water lines and a quick disconnect coupling to the endoscope supply cable. Water is "pumped" from the water bottle by supplying air under pressure through the air supply line to the top of this bottle.

The water bottle, which is substantially rigid, is refillable with fresh water by removing the cap.

Although the fresh water added to an endoscope water bottle may be sterile, the bottle itself may become contaminated during use by microscopic organisms which pass into the water bottle through the air or water supply tubes. Sterilization of supply tubes and the water bottle itself is thus desirable between each use. Not only is such sterilization time consuming for a physician's or hospital's staff, but failure to properly sterilize the tubes and the bottle results in a possible risk of patient infection.

SUMMARY OF THE INVENTION

It is an object of the present invention to provide a liquid supply system for use in an endoscope which reduces the time required to clean and sterilize the instrument.

It is another object of the present invention to provide a liquid supply system for use in an endoscope which reduces the risk of infection of a patient to an absolute minimum.

These objects, as well as further objects which will become apparent from the discussion that follows, are achieved, according to the present invention, by providing a disposable liquid supply system comprising a closed liquid container, a first flexible tube connected to the container and terminating at the top thereof for introducing a gas into the container, and a second flexible tube connected to the container and terminating at the bottom thereof for supplying a liquid to an endoscope. The container which contains a desired liquid, and the first and second tubes form a disposable, closed sealed unit which is connectable to an endoscope prior to use.

With a disposable unit of this type, a fresh supply of sterile water may be rapidly installed in the endoscope between each use with a patient. The servicing needs of the endoscope may therefore be reduced to a minimum.

The liquid supply system is preferably sealed at the factory to insure complete sterilization, thus minimizing the risk that the endoscope will transmit an infectious disease from one patient to another.

The liquid contained in the container may be sterile water, cleaning fluid, a sterilization fluid or any other liquid which may be required for the operation and servicing of an endoscope.

For a full understanding of the present invention, reference should now be made to the following detailed description of the preferred embodiments of the invention and to the accompanying drawings.

BRIEF DESCRIPTION OF THE DRAWINGS

FIGS. 10a, 10b and 10c are phantom, end and side views respectively, of a disposable connector, according to one preferred embodiment of the present invention, for use with the disposable liquid supply system of the present invention.

FIGS. 11a and 11b are end and side views, respectively, of a disposable connector according to another preferred embodiment of the present invention, for use with the disposable liquid supply system of the present invention.

DESCRIPTION OF THE PREFERRED EMBODIMENTS

The preferred embodiments of the present invention will now be described with reference to FIGS. 1-28 of the drawings.

Figure 1:
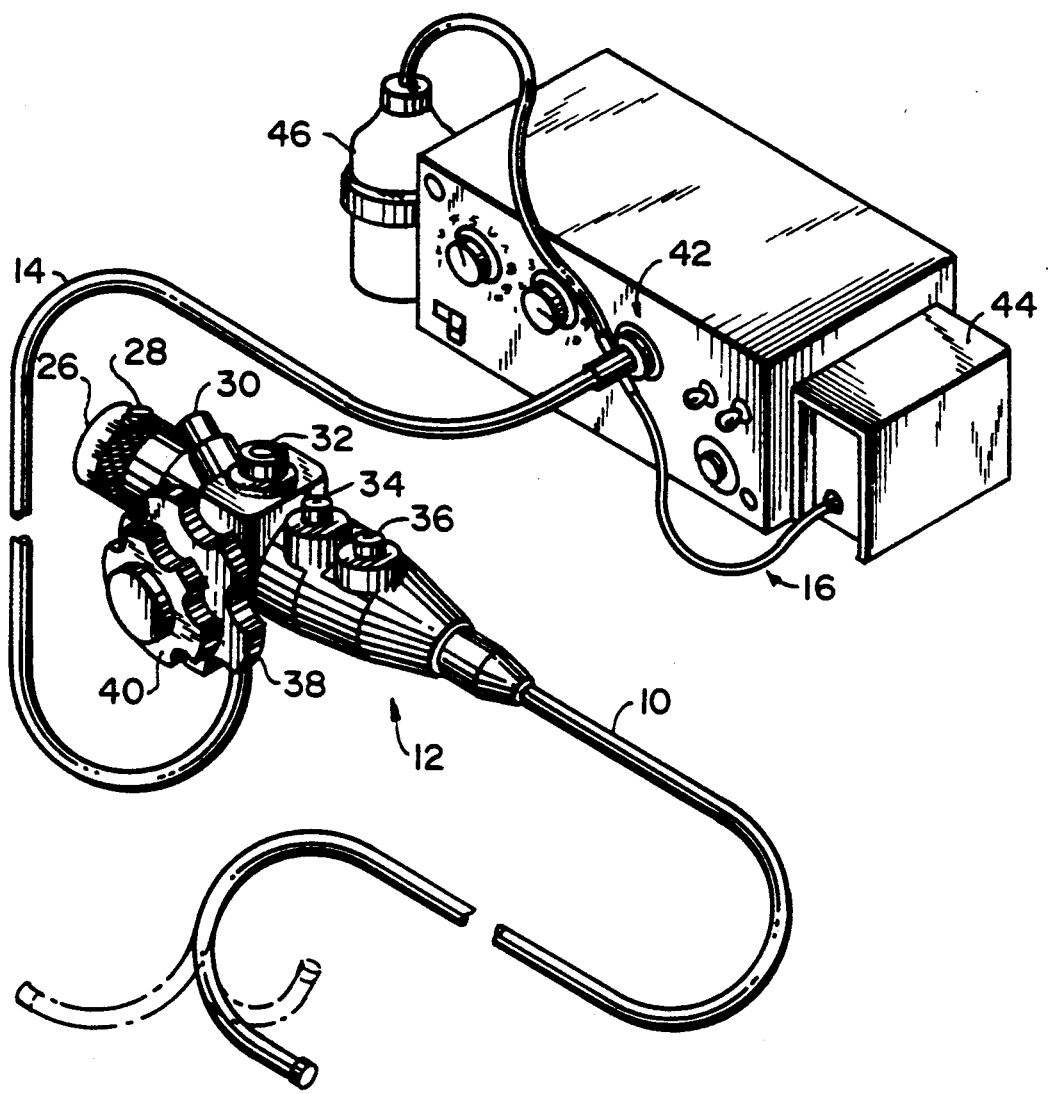
FIG. 1 is a perspective view of a typical endoscope having a flexible endoscope tube.
Figure 2:
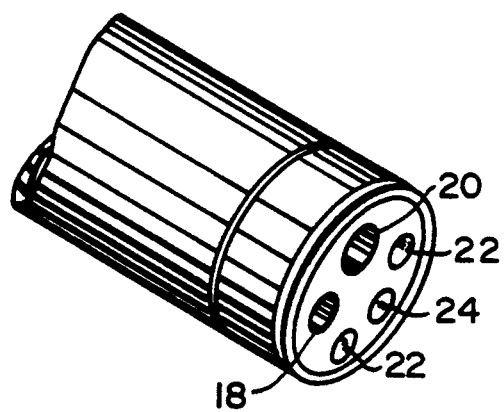
FIG. 2 is a perspective view of the distal end of the endoscope tube shown in FIG. 1.

FIG. 1 shows a typical gastrointestinal endoscope having a flexible endoscope insertion assembly tube 10, a tube control unit 12, connected to the endoscope tube 10, a flexible endoscope supply cable 14 connected to the tube control unit 12, and a base unit 16 connected to the supply cable 14. As may be seen in FIG. 2, which shows a magnified view of the tip of the endoscope tube 10, the endoscope tube includes a fluid (air/water) feed channel 18, an instrument and suction channel 20, fiberoptic light cables 22, and an image guiding system which, in this example, is a fiberoptic cable terminating in a fiberoptic viewing window 24.

The tube control unit 12 includes a viewing lens 26, a focus (adapter) ring 28, an instrument (forceps, snare) opening 30, a water feed button 32, an air feed button 34, a suction button 36, an up/down angle wheel 38, and a right/left angle wheel 40.

The flexible endoscope supply cable 14 includes a suction channel, a gas (air) feed channel and a liquid (water) feed channel. The base unit 16 is connected to the supply cable for applying suction to the suction channel and for supplying a gas and a liquid to the gas feed and liquid feed channels, respectively. The base unit includes a gas/liquid coupler 42 having a gas opening and a liquid opening connected to supply a liquid to the liquid feed channel of the supply cable. The base unit also includes a gas source (not shown), such as an air pump, to supply a gas to the gas opening of the gas/liquid feed coupler and to the gas feed channel of the supply cable. The base unit 16 further includes a light source (not shown), connected to a fiberoptic light cable within the supply cable and a suction pump 44 connected to the suction channel of the supply cable.

Finally, as shown in FIG. 1, the endoscope includes a liquid container 46 connected to the gas/liquid coupler 42 for supplying a liquid (e.g., water) to the liquid feed channel of the supply cable when a gas (e.g. air) is introduced into the container.

Figure 3:
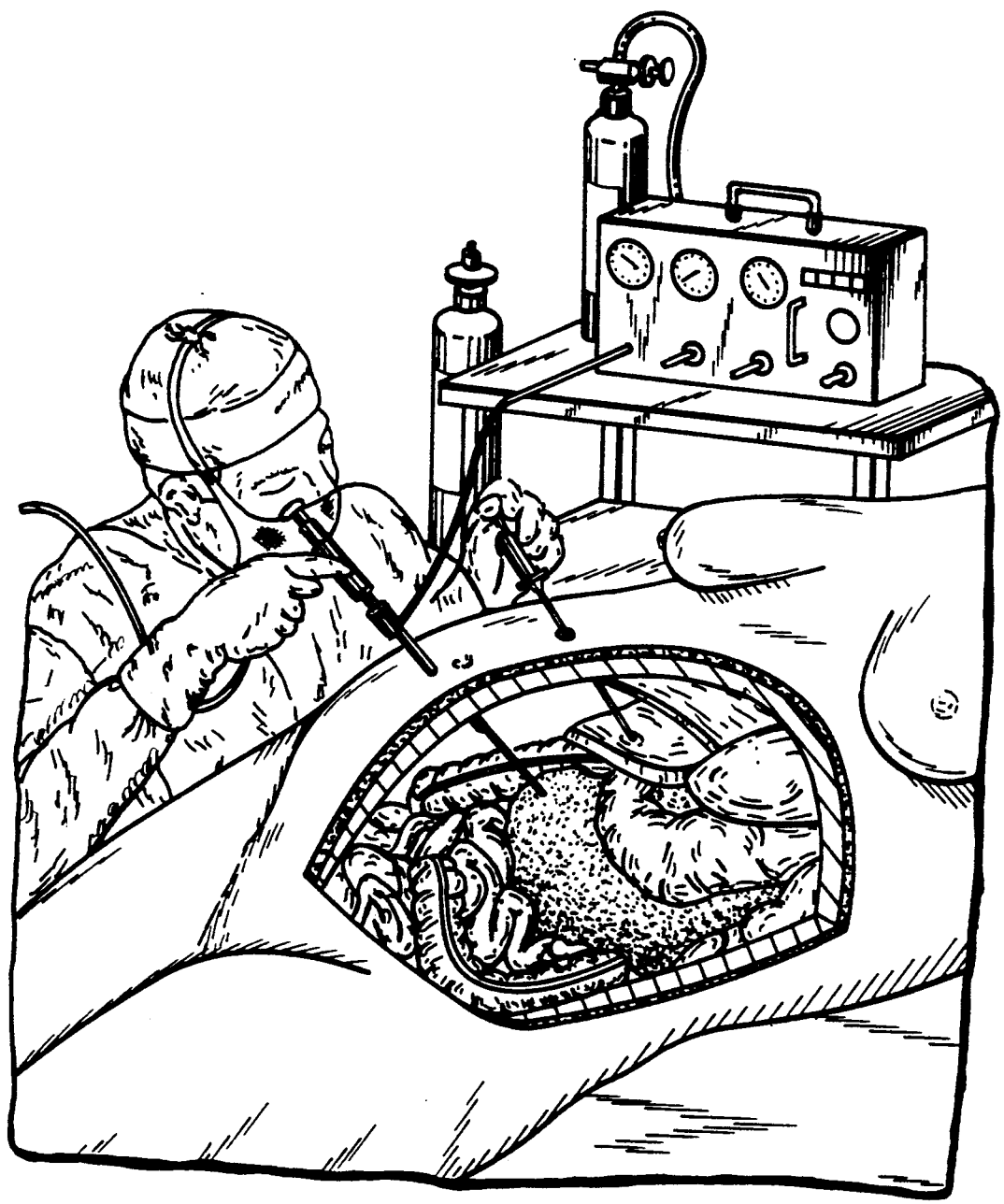
FIG. 3 is a perspective view of an endoscope having a rigid endoscope tube.

FIG. 3 illustrates another type of endoscope having a rigid endoscope tube. This instrument is similar in concept and design to that of FIG. 1, except that the rigid endoscope is intended for insertion into the abdomen of a patient just below or above the navel.

According to the present invention, an endoscope of this general type is provided with water, cleaning fluid or sterilization fluid by means of a disposable, sealed liquid supply system.

Figure 4:
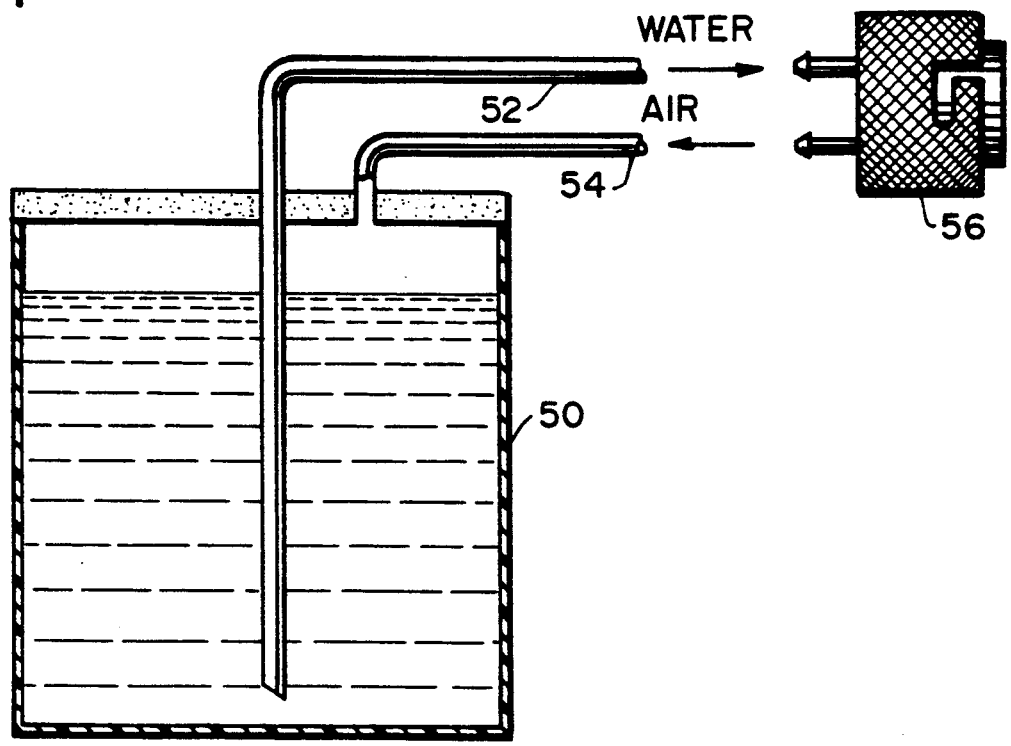
FIG. 4 is a diagrammatic representation of a disposable liquid supply system according to the present invention, for flexible and rigid endoscopy equipment.

FIG. 4 illustrates the general concept of a disposable liquid supply system according to the present invention. There is shown a heavy duty, heat sealed bag 50 with a long flexible tube for delivering a liquid and a short flexible tube 54 for delivering a gas (e.g. air) to the endoscope.

The inside of the bag is sterile and contains sterile water, cleansing fluid, sterilization fluid or some other liquid to be supplied to the endoscope. For simplicity, this liquid will hereinafter be referred to as "water".

Similarly the bag also contains a gas, such as air or carbon dioxide, above the water. For simplicity, this gas will hereinafter be referred to as "air". Both the air and water tubes are sealed and are designed to be cut prior to using; alternatively the tubes may be provided with removable caps.

The connector or adaptor 56 shown in FIG. 4 is made of metal or plastic and is designed to fit all makes of flexible and rigid, fiberoptic, video and lens type of endoscopic medical equipment. This adaptor has two connections: one for air out and the other for water in.

Use of the disposable water bottle/bag system according to the present invention in place of the standard, washable liquid supply system, insures that the liquid delivered will be absolutely sterile. The system according to the invention completely eliminates the possibility of cross contamination between patients, or the contamination of a patient by cleaning fluid. Since the water bottle/bag system is disposable, there is no need for an expensive, autoclavable bottle.

The water bottle/bag system is also advantageously used in places where sterile water is unavailable. The invention also eliminates the possibility of hard water build up of deposits in the air/water line or the nozzle.

Details of this inventive concept are shown in FIGS. 5-28.

Figure 5:
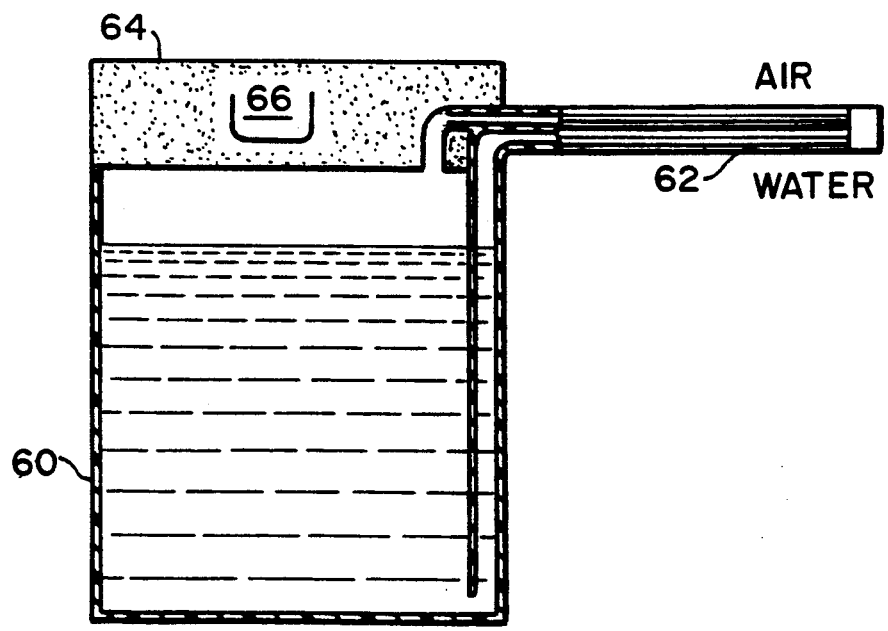
FIG. 5 is a diagrammatic representation showing one preferred embodiment of the liquid supply system of FIG. 4.

FIG. 5 shows a disposable water bag 60 with integrated air and water tubes 62. The approximate dimensions of the bag which contains 250 cc of sterile water is 180 cm×8 cm (7 inches×3¼ inches). The heat sealed top area of the bag is approximately 3 cm (1¼ inches) in width. This top area 64 has a cut out 66 which is approximately 2 cm×2 cm (¾ inches×¾ inches) in size, to enable the bag to be hung from the hook located on the side of all light sources of all types of endoscope equipment.

It is possible to bond the air tube and water tube which enter the top of the bag into the heat sealed area and to heat seal the bag in the manner shown to form the water tube. This makes it unnecessary to run a separate tube to the bottom of the bag, and thus reduces costs.

Figure 6:
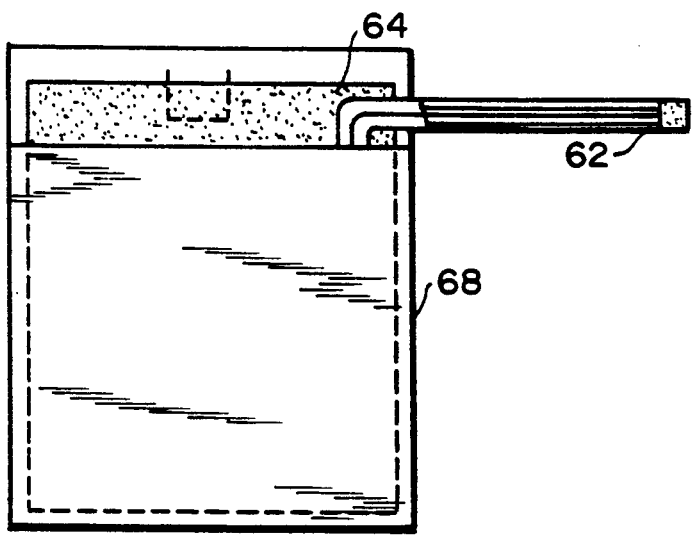
FIG. 6 is a diagrammatic representation showing a modification of the disposable liquid supply system of FIG. 5.

FIG. 6 illustrates a bag holder 68 which can be used to prevent the bag from expanding, if it is not made from a sufficiently rigid material. The pressure in the bag is 0.45–0.5 kg/cm$^2$ (6–8 pounds) approximately.

The holder 68 may be made of plastic or metal and has a hook to hang the holder onto the holder that is located on the side of the light source (or processor or ccu) of an endoscope.

Figure 7:
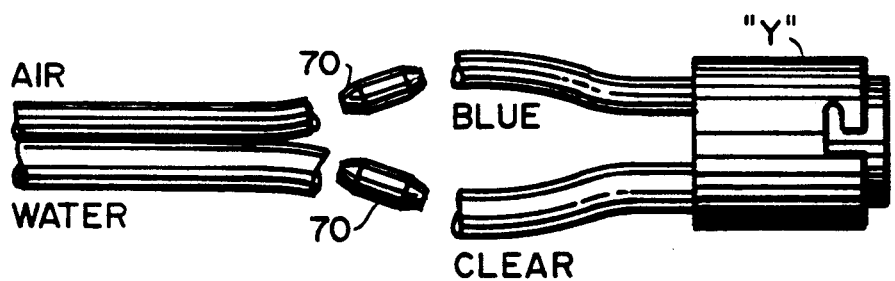
FIG. 7 is a detailed view of the flexible tubing in the embodiments of FIGS. 5 and 6 showing one preferred embodiment for connecting this tubing into an endoscope.

FIG. 7 illustrates a method of joining the air and water tubes from the disposable bottle or bag together with the air and water tubes from the endoscope water bottle connector "Y". This is accomplished by inexpensive, disposable "couplers" 70.

To make the connection easier, the tubes may be made of different sizes—for example a smaller for the air and a larger tube for water—and also may be color coded—for example blue for the water tube and clear for the air tube.

Figure 8:
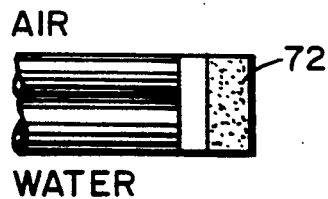
FIG. 8 is a detailed view of the end of the flexible tubing employed in the embodiments of FIGS. 5 and 6 showing one preferred embodiment for sealing the ends of the tubes.

FIG. 8 shows a device for closing and subsequently opening the tube. The device consists of a plastic member 72 bonded to the end of the tubes, which can be snapped off to open the tubes.

Figure 9:
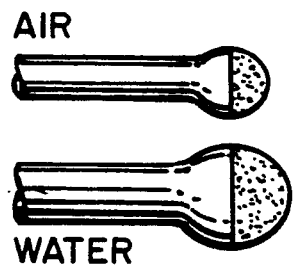
FIG. 9 is a detailed view of the end of the flexible tubing of FIGS. 5 and 6, showing an alternative embodiment for sealing the ends of the tubes.

FIG. 9 shows the ends of the tubes belled out and heat sealed. When cut, the taper allows the tube to be easily pressed on to the couplers, or onto the endoscope water bottle connector pipes.

It should be noted that the size of the bag is not critical and may be varied as desired to provide suitable amounts of cleaning solution and/or sterilizing solution for the endoscope.

FIGS. 10a, 10b and 10c show a design for a mass produced, injection molded Fujinon water bottle connector for the disposable water bottle/bag system.

The face "X" of the connector is made extremely flat so as to form an air and water tight seal. Depending upon the accuracy of the injection molded part, it may have to be machined.

The angled slot with the indent causes this connector to be pulled tightly against the water bottle connector on the flexible or rigid fiberscope or videoscope.

The tubes from the disposable water bottle/bag may be bonded onto the pipe stubs which project from this connector.

FIGS. 11a and 11b show a "cloverleaf" shaped, mass produced, injection molded design for a disposable connector for the disposable water bottle/bag system. Again, the face "X" of this connector is made very flat. The dashed lines, indicated as being "pre-stamped for bending" represent a crease, to allow easy bending, as shown.

The holes "Y" provide a tight fit onto the pins on the endoscope water bottle connector.

When mounting the connector, forward pressure is applied thereto and then the two appropriate ears are bent as shown to align and locate the connector onto the two water bottle connector pins on the endoscope connector.

Figure 12A:
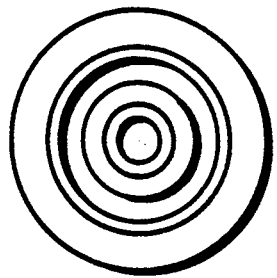
FIGS. 12a, 12b and 12c are end elevation, longitudinal section and vertical sectional views of still another disposable connector, according to a preferred embodiment of the present invention for use with the disposable liquid supply system of the present invention.
Figure 12B:
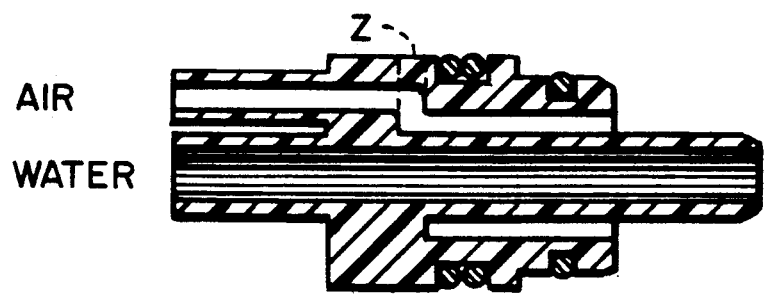
Figure 12C:
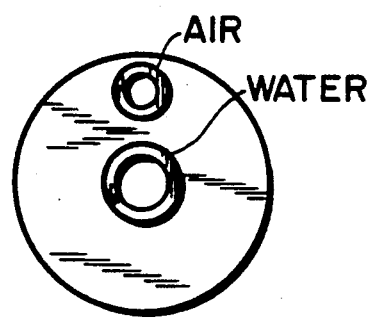

FIGS. 12a, 12b and 12c show a design for a mass produced, injection molded plastic/rubber connector for the Olympus and Pentax endoscopes for use with the disposable water bottle/bag system according to the present invention. This connector is injection molded in one piece if possible. Alternatively, the pipes for air and water may be bonded in. Also the hole "Z" may be drilled and then plugged.

The "O" rings shown may be eliminated if the connector is made from rubber or some other resilient type of material.

Figure 13:
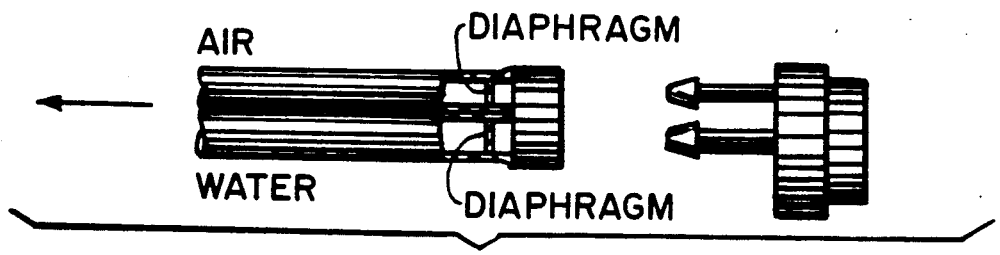
FIG. 13 is an elevational view showing the tube ends according to a preferred embodiment of the present invention designed for use with a standard connector.
Figure 14:
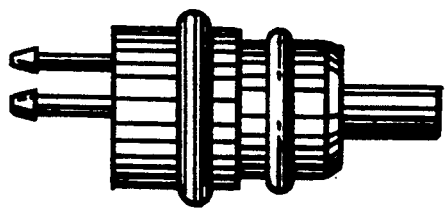
FIG. 14 is an elevational view of another standard connector used with an endoscope.

The air and water pipes from the disposable water bottle/bag may be bonded onto the air/water pipes which project out of this connector. In order to maintain sterility within the bag and for ease of transportation, the air and water tubes which emanate from the water bag may be provided with a diaphragm in their cuff, as shown in FIG. 13. The disposable connector (of either the Fujinon type or the Olympus/Pentax type) which is packaged in a sterile bag is provided with spiked connectors on the air and water pipe stubs, as shown in FIGS. 13 and 14.

Figure 15:
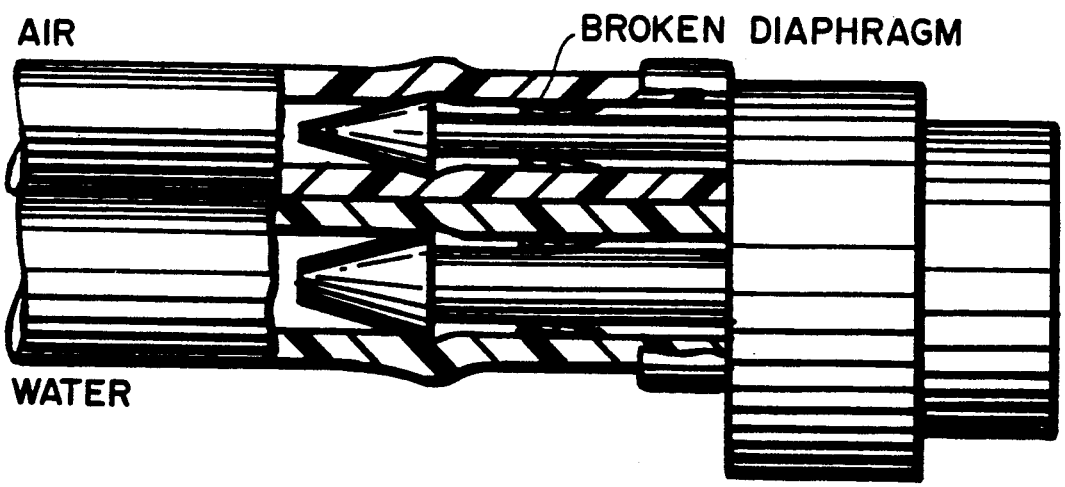
FIG. 15 is a detailed view showing how a standard connector is mated with the tube ends according to the present invention, so as to rupture diaphragms within the tube ends.

When the connector is removed from its sterile bag and attached to the water connector on the endoscope, the tubes from the disposable bag are then pushed onto the spiked connectors to break the diaphragm seals as shown in FIG. 15. The barbs on the spiked connectors form an air tight seal and prevent the tubes from pulling off.

The tubes, as well as the pipe stubs from the connector are of different sizes so that the air tube can only fit the air pipe, and the water tube can only fit the water pipe. In this way, if a water connector is attached to a bag, the operator knows that it has already been used for one patient, and it must therefore be disposed of.

Figure 16:
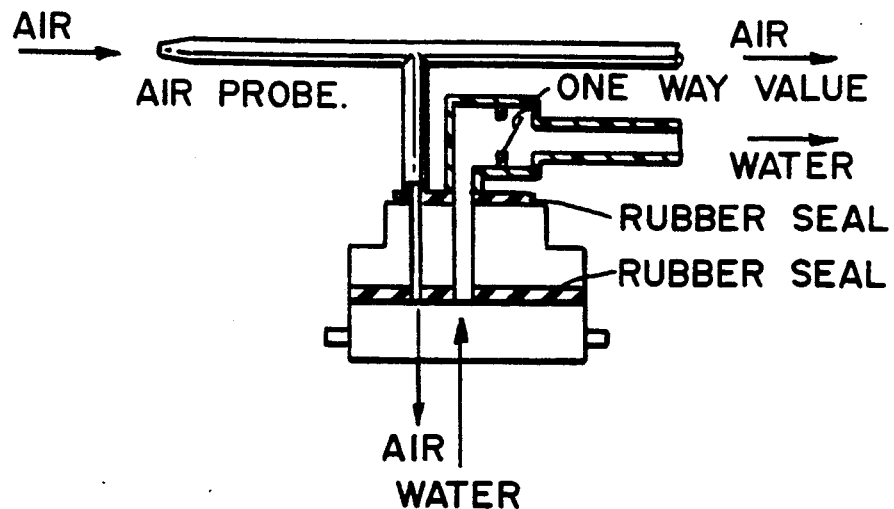
FIG. 16 is a diagrammatic representation of a non-return valve assembly for an endoscope water line according to one preferred embodiment of the present invention.
Figure 17:
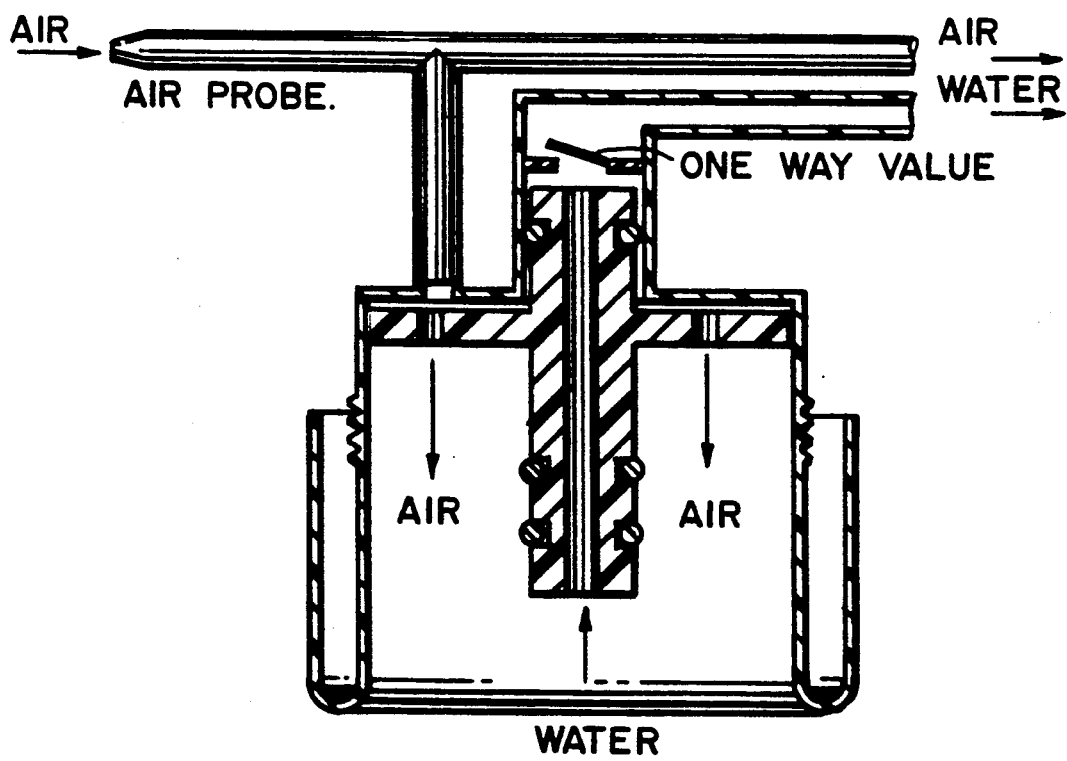
FIG. 17 is a diagrammatic representation of a non-return valve assembly for an endoscope water line according to another preferred embodiment of the present invention.

FIGS. 16 and 17 show non-return valve assemblies for the Fujinon water bottle connector and the Olympus/Pentax bottle connector, respectively. This device involves the fitting of a one way valve into the water line immediately behind the water bottle connector.

This arrangement prevents fluid from running back into the water bottle after the end of a medical procedure.

This device can be incorporated, as shown, into any flexible or rigid, fiberoptic or video endoscope of any make or design.

Figure 18:
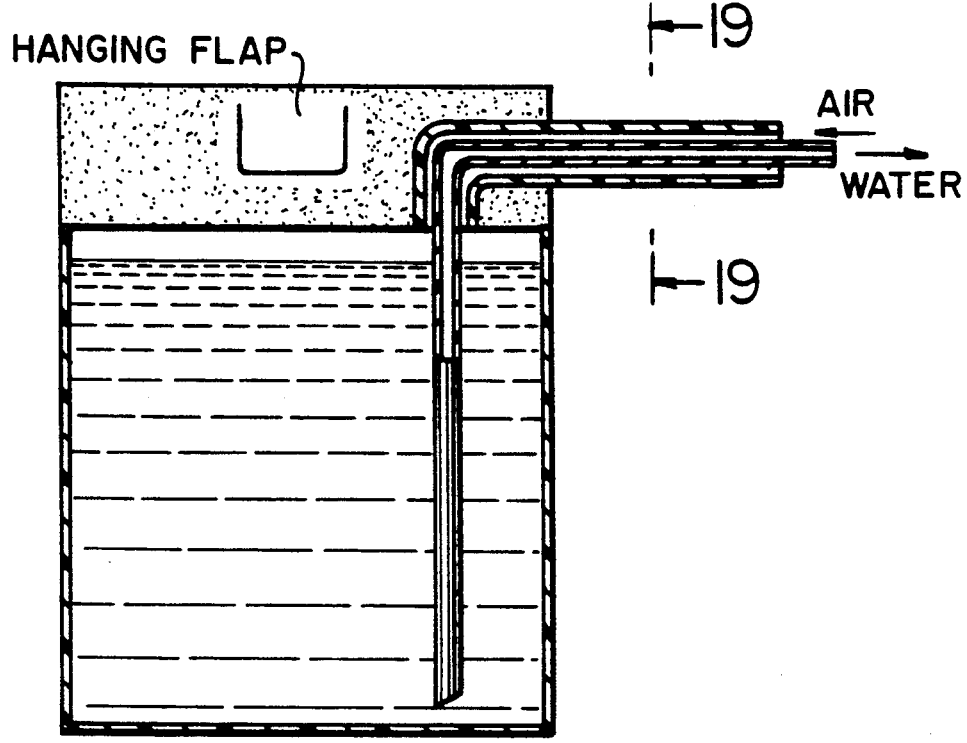
FIG. 18 is a diagrammatic representation showing a disposable liquid supply system according to the present invention in which the two feed tubes are concentrically arranged.
Figure 19:
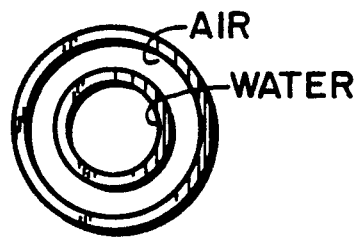
FIG. 19 is a cross-sectional view of the feed tubes employed with the disposable liquid supply system of FIG. 18.

FIGS. 18 and 19 show an embodiment of the disposable water bottle/bag system according to the invention wherein the water tube is contained within a larger diameter air tube. A gap is provided between the outside of the water tube and the inside of the air tube as indicated in FIG. 19. Air is pumped down the gap between the water tube and the air tube to pressurize the bottle/bag and to cause water to be forced up through the inner water tube.

Figure 20:
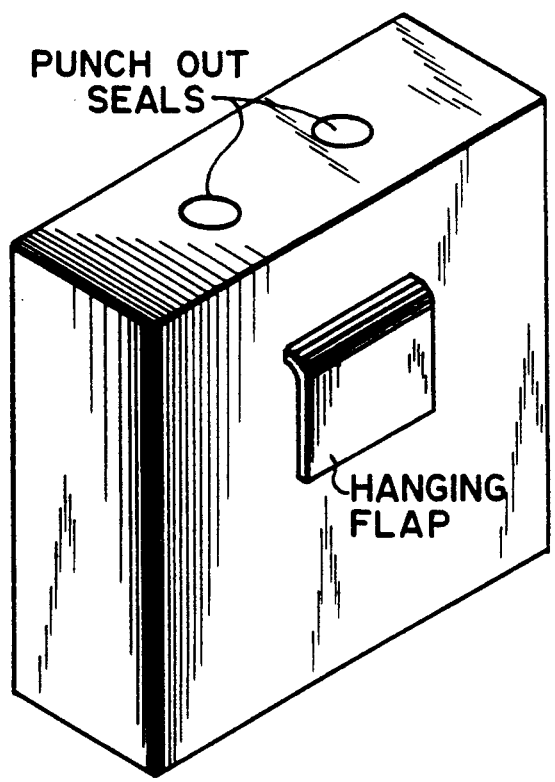
FIG. 20 is a perspective view of a disposable liquid supply system according to another embodiment of the present invention.
Figure 21:
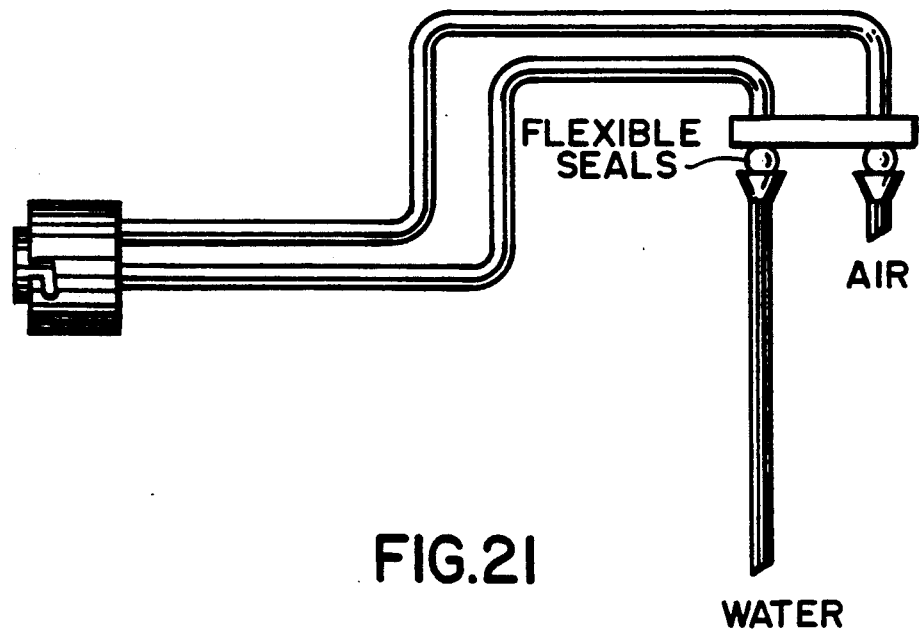
FIG. 21 is a side view of a disposable tubing system for use with the disposable liquid supply system according to the present invention.

FIGS. 20 and 21 shown still another embodiment of the disposable water bottle/bag system according to the present invention. This embodiment employs a cardboard box of wall thickness sufficient to withstand 0.35-0.5 kg/cm$^2$ of air pressure. The box is lined with either foil or plastic and fill with 250 cc of sterile water.

The top of the box is provided with two foil, plastic or other type of punch out seals. On the back of the box is a cardboard hanging flap of such dimensions as to enable it to be hung on all types of endoscope light sources.

FIG. 21 shows the flexible, disposable air/water supply tube assembly. This consists of the disposable connector for Fujinon, Olympus and Pentax on one end. On the other end are arranged two rigid tubes, one long tube which is designed to reach to the bottom of the box for supplying water and one short tube for supplying air.

These tubes, which are made of a rigid plastic, are molded into a top plate. The ends of the tubes are angled and pointed to facilitate puncturing the seals on the top of the box.

At the top of the tubes are tapered barbs to prevent the tubes from being withdrawn from the box. Immediately behind the barbs are flexible seals to keep the box airtight.

The box may also be permanently fitted with tubes which are capped at their ends.

Figure 22:
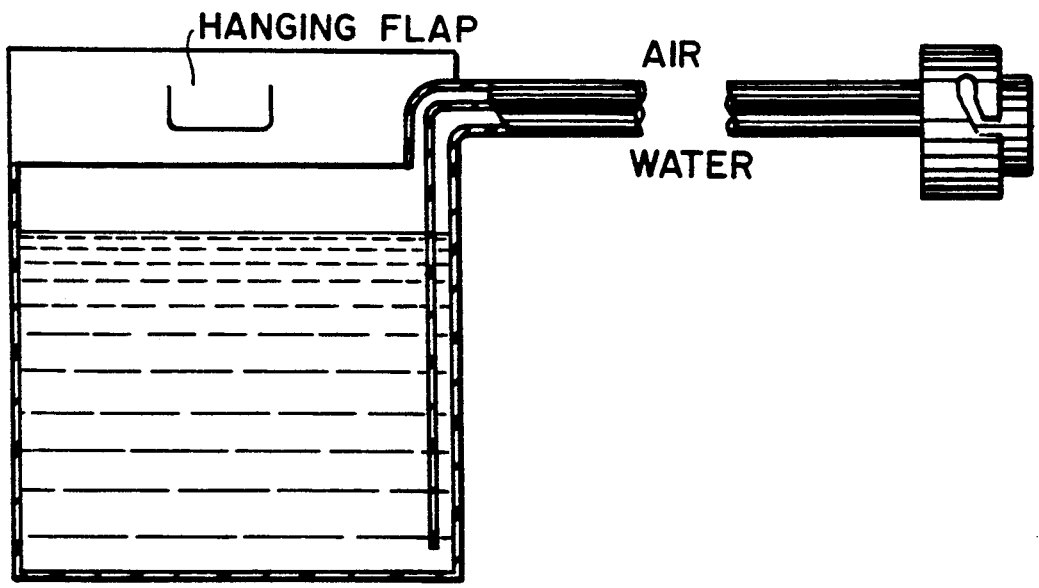
FIG. 22 is a representational diagram of a disposable liquid supply system according to the present invention together with a disposable connector.
Figure 23:
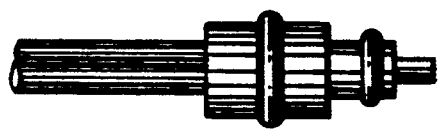
FIG. 23 is an elevational view of another disposable connector which may be used with the disposable liquid supply system of FIG. 22.
Figure 24:
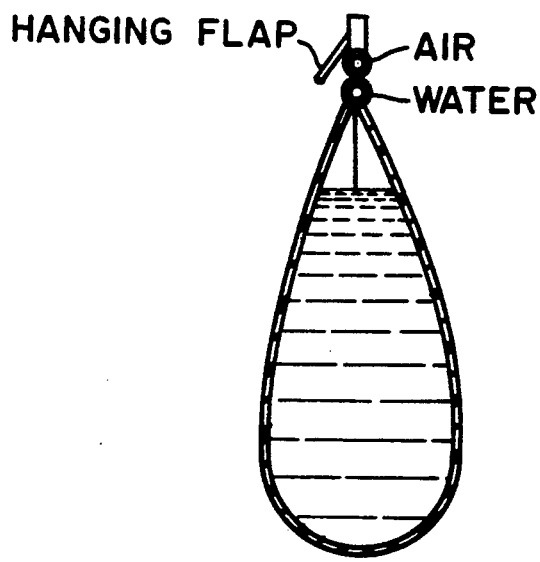
FIG. 24 is a side view of the disposable liquid supply system of FIG. 22.
Figure 25:
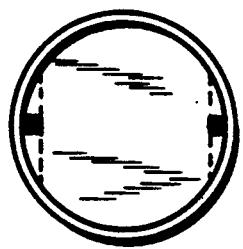
FIGS. 25 and 26 are end and side views, respectively, of a cap which fits over the end of the disposable connector of FIG. 22.
Figure 26:
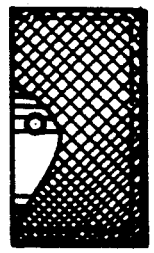
Figure 27:
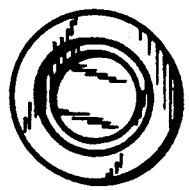
FIGS. 27 and 28 are end and side views, respectively, of a cap which fits over the end of the disposable connector of FIG. 23.
Figure 28:
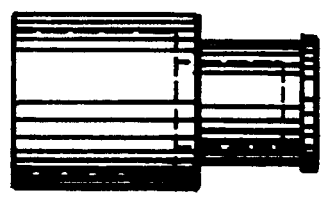

FIGS. 22, 23 and 24 illustrate a production disposable water bottle/bag system according to the present invention. FIG. 22 shows the flexible bag RF welded on all four sides with the top portion RF welded in a band approximately 3 cm deep. Down the right hand side of the bag is an RF welded seam stopping short of the bottom of the bag, thus creating a tube approximately 4 mm across.

The outer bag dimensions are approximately 10 cm $\times$ 10 cm, or of an appropriate size to hold 250 cc of sterile water.

Into the top of the bag are cemented/glued two tubes having the same dimension of 4 mm outer diameter and 3 mm inner diameter. These tubes are made of a flexible material and are approximately 4 cms long.

The air tube is shorter than the water tube and stops at the junction of the RF welded top portion of the bag. The other tube is cemented/glued into the top of the tube created down the right side of the bag.

In the top of the RF welded portion of the bag, an area of approximately 2 cm $\times$ 2 cm is cut on three sides to create a flap, which will enable the bag to be hung onto any existing light source.

The other ends of the two flexible tubes are cemented/glued to either one of two disposable connectors, depending upon which endoscope instrument the bag is to be connected. One connector, shown in FIG. 22, serves for connection to a Fujinon scope; the other connector is designed to be connected to an Olympus, Pentax or Acmi instrument.

The connectors are designed to mass produced by injection molding, or some other method, and are made of a semi-rigid or rigid material.

FIGS. 25-28 illustrate caps which are designed to fit over the reflectors of FIGS. 22 and 23, respectively, to maintain the sterility of the whole system and also to prevent the fluid inside of the bag from leaking out.

The bag employed with the disposable water bottle/bag system according to the invention must be made of a material which is rigid enough, or has horizontal threads or seams therein to prevent the bag from splitting during pressurization. The bag must also be able to withstand the temperatures incurred during sterilization in manufacture.

The bag can also be provided with a third tube, which is used for filling the bag with sterile water during production. After filling, this third tube may be sealed to close it permanently.

Since the bag is disposable, a one way valve or valves may be fitted onto the air/water tubes to prevent refilling and reuse. Alternatively, the connectors may be made to destruct when they are removed from the endoscope.

There has thus been shown and described a novel disposable liquid supply system for an endoscope which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention which is limited only by the following claims.

What is claimed is:

1. An endoscope comprising, in combination:
    (a) an endoscope insertion assembly tube having first and second ends, said tube including:
        (1) a fluid feed channel;

(2) an instrument and suction channel;
(3) a fiberoptic light cable; and
(4) an image guiding system;
(b) a tube control unit connected to said first end of said endoscope tube;
(c) a flexible endoscope supply cable having first and second ends, said first end of said supply cable being connected to said tube control unit, said cable including:
(1) a suction channel;
(2) a gas feed channel; and
(3) a liquid feed channel;
(d) a base unit connected to said second end of said supply cable for applying suction to said suction channel and for supplying a gas and a liquid to said gas feed and liquid feed channels, respectively, said base unit including:
(1) a gas/liquid coupler having a gas opening and a liquid opening connected to supply a liquid to said liquid feed channel of said supply cable; and
(2) a gas source connected to supply a gas to said gas opening of said gas/liquid feed coupler and to said gas feed channel of said supply cable;
(e) a liquid supply system including:
(1) a liquid container having a top and a bottom;
(2) a first tube connected between said top of said container and said gas opening of said gas/liquid coupler for introducing a gas into said container; and
(3) a second tube connected between said bottom of said container and said liquid opening of said gas/liquid coupler for supplying a liquid to said liquid opening and thus to said liquid feed channel of said supply cable; and
(f) a one-way valve arranged along a liquid path between said liquid container and said second end of said endoscope tube, for permitting liquid to pass in the direction toward said second end of said endoscope tube but not in the reverse direction toward said liquid container.

2. The endoscope defined in claim 1, wherein said one-way valve is arranged in said gas/liquid coupler.

3. The endoscope defined in claim 2, wherein said one-way valve is a flap valve having a valve seat, a flap arranged on said seat which is hinged for movement with respect thereto.

4. The endoscope defined in claim 2, wherein said one-way valve is a ball check valve having a valve seat, a ball arranged on said seat, and means for biasing said ball toward said seat.

5. The endoscope defined in claim 1, wherein said liquid supply system is a sealed disposable unit.

6. The endoscope defined in claim 1, wherein said insertion assembly tube is flexible, whereby said endoscope is a flexible endoscope.

7. The endoscope defined in claim 1, wherein said insertion assembly tube is rigid, whereby said endoscope is a rigid endoscope.

8. An endoscope comprising, in combination:
(a) an endoscope insertion assembly tube having two ends, said tube including:
(1) a fluid feed channel;
(2) an instrument and suction channel;
(3) a fiberoptic light cable; and
(4) an image guiding system;
(b) a tube control unit connected to one end of said endoscope tube;
(c) a flexible endoscope supply cable having first and second ends, said first end of said supply cable being connected to said tube control unit, said cable including:
(1) a suction channel;
(2) a gas feed channel; and
(3) a liquid feed channel;
(d) a base unit connected to said second end of said supply cable for applying suction to said suction channel and for supplying a gas and a liquid to said gas feed and liquid feed channels, respectively, said base unit including:
(1) a gas/liquid coupler having a gas opening and a liquid opening connected to supply a liquid to said liquid feed channel of said supply cable; and
(2) a gas source connected to supply a gas to said gas opening of said gas/liquid feed coupler and to said gas feed channel of said supply cable; and
(e) a disposable liquid supply system including:
(1) a closed liquid container having a top and a bottom;
(2) a first flexible tube connected between said top of said container and said gas opening of said gas/liquid coupler for introducing a gas into said container; and
(3) a second flexible tube connected between said bottom of said container and said liquid opening of said gas/liquid coupler for supplying a liquid to said liquid opening and thus to said liquid feed channel of said supply cable;
said container and said first and second tubes forming a sealed unit which is connectable to said gas/liquid coupler.

9. The endoscope defined in claim 8, wherein said liquid is sterile water.

10. The endoscope defined in claim 8, wherein said liquid is a cleaning fluid.

11. The endoscope defined in claim 8, wherein said liquid is a disinfecting solution.

12. The endoscope defined in claim 8, wherein said first and second tubes are connected together in parallel.

13. The endoscope defined in claim 12, wherein said first and second tubes are separate, individual tubes.

14. The endoscope defined in claim 12, wherein said first and second tubes are formed of an integral tube structure with two longitudinal openings.

15. The endoscope defined in claim 8, wherein one of said first and second tubes is arranged inside of the other.

16. The endoscope defined in claim 8, wherein said first and second tubes are closed at their free ends.

17. The endoscope defined in claim 16, wherein said first and second tubes each include a frangible diaphragm at its free end which closes the respective tube opening and which may be broken when the free end of the respective tube is forced over a rigid pipe stem.

18. The endoscope defined in claim 16, wherein said first and second tubes are heat-sealed at their free ends.

19. The endoscope defined in claim 18, wherein said container is a rigid bottle.

20. The endoscope defined in claim 18, wherein said container is a flexible bag.

21. The endoscope defined in claim 20, wherein said bag is made of a translucent plastic.

22. The endoscope defined in claim 20, wherein said bag includes a flap at said top thereof to facilitate holding.

23. The endoscope defined in claim 22, wherein said flap has an aperture to facilitate hanging.

24. The endoscope defined in claim 20, wherein said bag is substantially flat and rectangular in shape.

25. The endoscope defined in claim 20, further comprising a bag holder having a pouch for supporting said flexible bag.

26. The endoscope defined in claim 16, wherein said first and second tubes are flared outward at their free ends to facilitate sliding onto rigid pipe stems.

27. The endoscope defined in claim 8, further comprising an adapter connected to the free ends of said first and second tubes, for connection to the gas/liquid coupler of an endoscope.

28. The endoscope defined in claim 8, further comprising an adapter for connection to the free ends of said first and second tubes and to the gas/liquid coupler of an endoscope.

29. The endoscope defined in claim 28, wherein said first and second tubes each include a frangible diaphragm at its free end which closes the respective tube opening and which may be broken when the respective tube is forced over a rigid pipe stem and wherein said adaptor has a rigid pipe stem protruding therefrom for insertion, respectively, in the free end of said first and second tubes.

30. The endoscope defined in claim 8, further comprising a one-way valve in said second tube, permitting liquid to exit from said container, but not to enter it.

31. The endoscope defined in claim 8, wherein said insertion assembly tube is flexible, whereby said endoscope is a flexible endoscope.

32. The endoscope defined in claim 8, wherein said insertion assembly tube is rigid, whereby said endoscope is a rigid endoscope.

* * * * *